(12) United States Patent
Goehde

(10) Patent No.: US 8,049,888 B2
(45) Date of Patent: Nov. 1, 2011

(54) DEVICE FOR MEASURING LIGHT EMITTED BY MICROSCOPICALLY SMALL PARTICLES OR BIOLOGICAL CELLS

(75) Inventor: Wolfgang Goehde, Nottuln (DE)

(73) Assignee: Firma Cytecs GmbH, Goerlitz (DE)

( * ) Notice: Subject to any disclaimer, the term of this patent is extended or adjusted under 35 U.S.C. 154(b) by 657 days.

(21) Appl. No.: 11/573,024

(22) PCT Filed: Mar. 1, 2004

(86) PCT No.: PCT/DE2004/000394
§ 371 (c)(1),
(2), (4) Date: Nov. 3, 2008

(87) PCT Pub. No.: WO2005/085803
PCT Pub. Date: Sep. 15, 2005

(65) Prior Publication Data
US 2009/0140168 A1 Jun. 4, 2009

(51) Int. Cl.
*G01J 1/58* (2006.01)
*G01N 21/00* (2006.01)
(52) U.S. Cl. ........ 356/338; 356/336; 356/337; 356/432; 250/483.1
(58) Field of Classification Search .......... 356/335–343, 356/246, 244, 432–444, 39; 250/458.1, 573–575, 250/222.2, 483.1; 359/189; 422/82.11, 82.05
See application file for complete search history.

(56) References Cited

U.S. PATENT DOCUMENTS

| | | | | |
|---|---|---|---|---|
| 3,710,933 A * | 1/1973 | Fulwyler et al. | ............... | 209/3.1 |
| 4,553,034 A * | 11/1985 | Byers et al. | ................ | 250/458.1 |
| 4,746,179 A * | 5/1988 | Dahne et al. | .................... | 385/12 |
| 5,082,629 A * | 1/1992 | Burgess et al. | ............ | 422/82.11 |
| 5,269,937 A * | 12/1993 | Dollinger et al. | ............ | 210/656 |
| 5,475,487 A * | 12/1995 | Mariella et al. | ............... | 356/336 |
| 5,568,304 A * | 10/1996 | Baur | ............................ | 398/202 |
| 5,701,012 A * | 12/1997 | Ho | ............................ | 250/461.2 |
| 5,822,062 A * | 10/1998 | Kusuzawa | ..................... | 356/343 |
| 6,154,276 A * | 11/2000 | Mariella, Jr. | .................. | 356/337 |
| 6,452,676 B1* | 9/2002 | Kawamura | ..................... | 356/338 |
| 6,661,510 B1* | 12/2003 | Hanning et al. | ............. | 356/318 |
| 6,867,857 B2* | 3/2005 | Hobbs | .......................... | 356/246 |
| 7,064,823 B2* | 6/2006 | Roche et al. | .................. | 356/246 |
| 7,170,601 B2* | 1/2007 | Matsuda | ....................... | 356/336 |
| 7,436,515 B2* | 10/2008 | Kaye et al. | .................... | 356/436 |

* cited by examiner

*Primary Examiner* — Sang Nguyen
(74) *Attorney, Agent, or Firm* — Greenblum & Bernstein, PLC

(57) ABSTRACT

With a device for measuring the fluorescent light or scattered light emitted by microscopically small particles or cells (12), with a flow-through cuvette (8) through which the luminescent particles or cells (12) are guided, whereby the flow-through cuvette (8) has a transparent window (3), and with a photodetector (2), which records the light emitted by the luminescent particles or cells (12), and with an optical element that guides the light emerging from the window (3) to the photodetector (2), the invention suggests that the optical element is embodied as a cylinder (4, 9) with a cylindrical reflecting surface.

14 Claims, 3 Drawing Sheets

Figure 1:
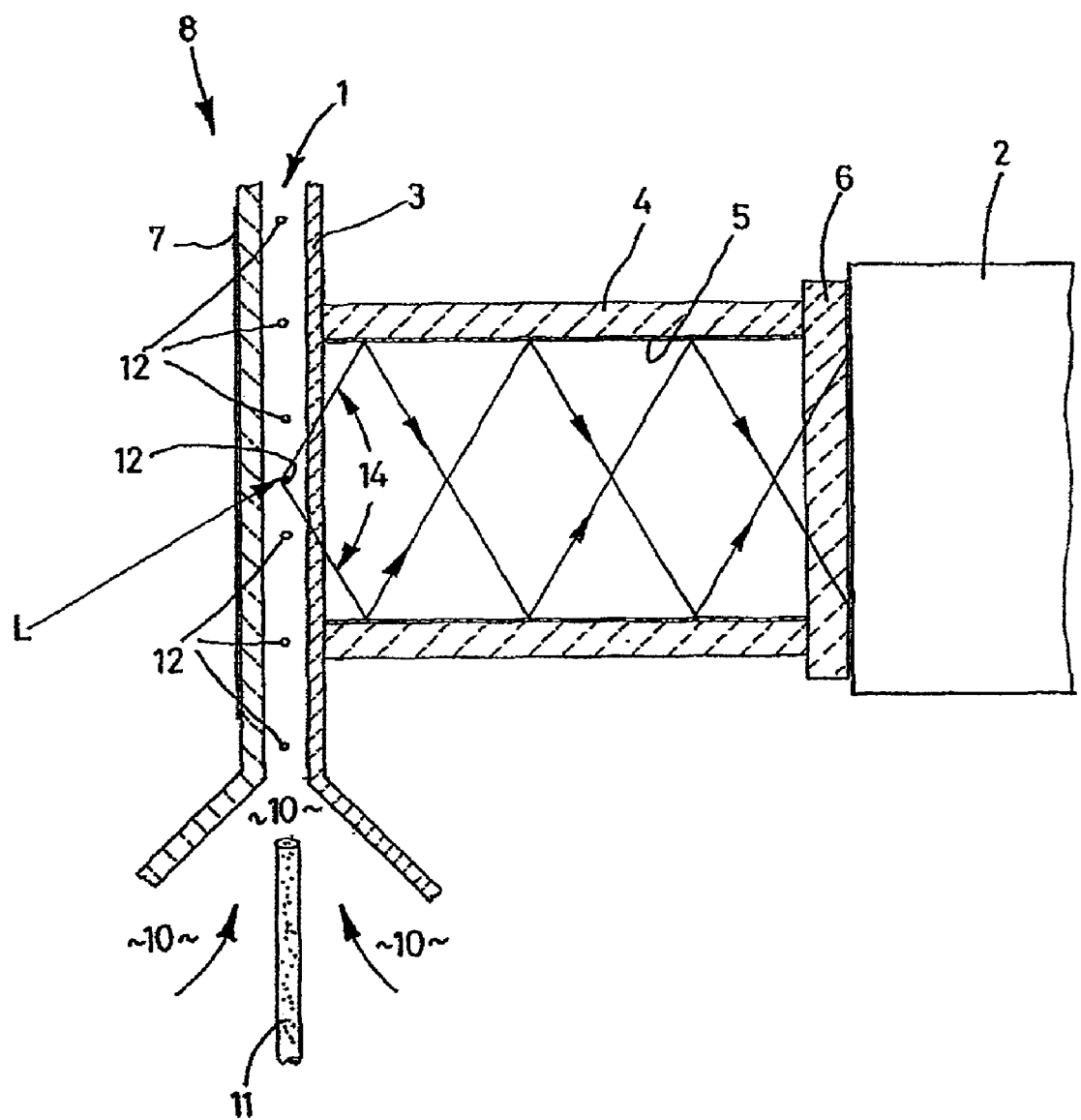

DEVICE FOR MEASURING LIGHT EMITTED BY MICROSCOPICALLY SMALL PARTICLES OR BIOLOGICAL CELLS

Methods are known for the characterization of microscopically small particles or biological cells, in which methods these particles are guided in suspension through an intense light beam, e.g., of a laser. The light scattered by the particles is received at different angles and recorded and measured by means of sensitive photodetectors. In order to differentiate between different cell types, the cells are marked by means of special fluorescent dyes. Different cells can be stained with different markers. If these cells pass the light beam for fluorescence excitation, they emit fluorescent light that is recorded and quantified likewise by means of photodetectors. In this manner it is possible to differentiate from one another and count, e.g., different blood cells or leucocytes in a single measuring process.

This method known under the term "flow cytophotometry" or "flow cytometry" has become widely used in medical diagnostics. It serves, e.g., for automated cancer cell recognition, the quantification of leucocyte subpopulations and the evaluation of the immune status of HIV/AIDS patients by recording and counting the leucocytes responsible for immune defense. In addition, these methods serve as analytical methods using microscopically small plastic particles to which the biochemical substances to be measured, such as nucleic acids and proteins, are bonded together with fluorescent dyes. The use in the context of flow cytophotometry is mentioned below in a simplified manner and representing other possible applications.

The metrological task is to effectively record the very small amounts of light emitted by cells or particles of such smallness. The cells or particles move through the light beam very rapidly, so that it is possible to measure as many of them as possible within a short time. Modern flow cytometers record more than 10,000 individual particles per second with dwell times in the light beam of below 10 μsec. In terms of metrology this means that the integration times for the light measurement are very short.

It is rendered possible to ensure a sufficient measuring sensitivity anyway in that the light emitted by the particles is recorded by microscope lenses that have a high numerical aperture, so that a high share of the light is recorded. Optical elements are thus used between a flow-through cuvette and a photodetector, which elements are to supply to the photodetector the highest possible share of the light emitted by the cells. All flow cytophotometers known in practice use similar lenses with high numerical aperture to record the largest possible solid angle and thus the highest possible share of the fluorescent light emitted by the cells, since the light is not reflected by the particles in a particular direction, but released in a spherical manner. The fluorescent light reaches the photoelectric receiver or several photoelectric receivers via optical elements, lens systems and intermediate images arranged downstream.

It is characteristic of these known optical arrangements that the optical systems used require a very precise optical image of the measuring point or the cell to be measured because of the low focus depth associated with the high numerical aperture. This leads to high demands on the precision of the components, the mechanical stability of the entire measuring arrangement and thus to a considerable adjustment complexity. The correspondingly high sensitivity of these measuring systems does not allow, e.g., mobile use, e.g., in mobile laboratories for the microbiological monitoring of bodies of water or for determining as a part of therapy the immune status of HIV/AIDS patients in regions without any basic medical care or without laboratory infrastructure.

The object of the invention is to improve a generic device by embodying it to be rugged while maintaining measuring sensitivity and measuring precision and by making it suitable for use in mobile laboratories, and by making it possible for the maintenance expenditure, the amount of adjustment interventions and the susceptibility to damage to be reduced or completely eliminated.

This object is attained by a device with the features of claim 1.

In other words, the invention suggests embodying the optical element as a cylinder with a cylindrical reflecting surface. Instead of a complicated structure containing several optical lenses, a rugged, one-piece optical element is used that does not require any adjustment or maintenance at all. Within the scope of the present suggestion, cylinder thereby means, as explained below, both solid and also hollow bodies. The cross-sectional shape of a cylinder of this type is preferably circular, e.g., because of manufacturing advantages; but the advantages according to the suggestion also arise with cross sections shaped in a manner deviating from a circle, e.g., ovaloid or polygonal cross sections. The cylindrical reflecting surfaces produce a tunnel for the light through which it goes from the flow-through cuvette to the photodetector virtually without any loss.

Apart from an improved ruggedness, the suggested embodiment of the device renders possible further advantages:

Improved Sensitivity of the Device:

The suggested arrangement allows the measurement of the smallest amounts of light emitted by microscopically small particles or cells. Compared to the prior art, this new arrangement does not require any lenses or complicated lens systems. The disadvantages of the lenses with high numerical aperture otherwise required and the high adjustment complexity associated therewith are thus eliminated. The suggested arrangement requires considerably fewer optical interfaces. This causes fewer light losses and thus greater measuring sensitivity.

A correspondingly large diameter of the light-collecting cylinder makes it possible to ensure that the share of light that can be recorded metrologically at all reaches the light-collecting cylinder, i.e., the space enclosed by the cylindrical reflecting surface, as completely as possible. This is linked to the fact that the solid angle of the fluorescent light to be recorded is essentially determined by the total reflection angle at the interfaces of liquid and glass wall in the cuvette channel and cuvette window. Only the share of the spherically emitted fluorescent light emitted within this solid angle can go from the flow-through cuvette to the photodetector. Purely by way of example, the diameter of the cylindrical reflecting surface can be approximately 50 times bigger or even larger than the minimum distance between the light-emitting particle and the light entrance opening of the cylinder.

Compared to the prior art, a further advantage of the suggested arrangement is the fact that a larger solid angle and thus a greater share of the fluorescent light emitted is recorded than is possible with a conventional optical lens system. If the cylinder is embodied, e.g., not as a hollow cylinder, but as a solid body, and if it is made of glass, it is connected to the flow-through cuvette or to its window preferably by means of an optical putty. The solid angle of the recorded light is thus enlarged considerably again. This is because there are fewer losses through reflection at interfaces, which losses cannot be avoided with conventional lens options.

Simpler Assembly and Startup of the Device:

Compared to an optical lens system, first, the number of the components required is reduced so that, first of all, the production of the device is simplified in principle.

Secondly, if the diameter of the cylindrical reflecting surface is enlarged even more than stated above, it is possible for the share of light corresponding to the greatest possible solid angle to reach the light-collecting cylinder as completely as possible, even if the particle to be measured is not located optimally close to the light entrance opening of the cylinder, so that the distance from the light-collecting cylinder is noncritical, similar to an enlarged focus depth range of an optical lens system. Advantageously, the diameter of the cylindrical reflecting surface of the cylinder is thus comparatively large. As a result, the position of the particle to be measured perpendicular to the observation direction is noncritical as well, namely advantageously over the entire width of the cuvette channel, so that all the light-emitting particles or cells can reliably be recorded metrologically with maximum luminous efficacy. Irrespective of the position of the particle, it is always the same solid angle of the fluorescent light, i.e., the same share of the fluorescent light radiated spherically overall, that reaches the light-collecting cylinder or tunnel. The sensitive adjustment of the measuring cell with respect to the photodetector can thus be omitted.

Simple Operability of the Device:

The suggested device for the light recording of microscopic particles does not require readjustment or complex optical adjustment, namely neither during setup nor later on during operation. All the components are permanently connected to one another in a fixed manner. As a result, the arrangement is insensitive to vibrations and sufficiently rugged to render possible use in mobile laboratories. The suggested device thus opens up completely new fields of application of flow cytophotometry, in which fields the arrangements hitherto known could not be used because of their sensitivity. For instance, an immunodiagnosis accompanying the therapy of HIV/AIDS patients in rural areas of the poorest countries is thus rendered possible.

In particular if, as mentioned previously, the diameter of the cylinder is large, the advantages of a so-called "high numerical aperture" arise, as are known from optical lens systems in principle, but are not realized with generic devices, and as cannot be achieved with customary so-called optical waveguides made of optical fibers, since these waveguides have a considerably lower numerical aperture.

Exemplary embodiments of the invention are explained in more detail below on the basis of the purely diagrammatical drawings. They show FIG. 1 A first exemplary embodiment with a measuring device featuring a hollow cylinder, FIG. 2 A second exemplary embodiment, in which two measuring devices similar to that of FIG. 1 are provided, and FIG. 3 A third exemplary embodiment with a measuring device featuring a solid cylinder.

The drawings always represent a highly schematized section of a flow cytophotometer. FIG. 1 shows that two partial flows (respectively indicated by arrows) of a transport fluid 10 merge in a manner known per se above a tubule 11. Fluorescently marked cells 12 to be counted emerge individually at the top end of the tubule 11 and are transported through an interior channel 1 of a flow-through cuvette 8 of the device together with the transport fluid 10. There they are irradiated by a thin laser beam and excited to emit fluorescent light. In the drawing, the laser beam runs perpendicular to the drawing plane; it is therefore discernible merely as a point impinging on a cell 12 and marked by an arrow labeled L. The width of the interior channel 1 discernible from FIG. 1 is so small that the cells 12 enter into the laser beam individually and create individual, distinguishable and thus countable light pulses.

The interior channel 1 is closed off by a glass wall in the form of a thin-walled window 3 in the direction of a photon receiver or photodetector 2. Typically, the wall thickness is 0.2 to 1 mm. A hollow cylinder 4 with an interior diameter of typically 8 to 10 mm, a diameter that is large compared to the width of the interior channel 1, rests on this window 3. The interior wall surface of the hollow cylinder 4 is mirrored, so that a cylindrical reflecting surface for the fluorescent light entering the hollow cylinder 4 is the result. In favor of the ruggedness of the entire device, the hollow cylinder 4 can be made of metal, but other materials are possible as well, whereby those materials are preferably used that render possible a very smooth surface. Depending on the material used, its interior wall surface can be polished, so that the material of the hollow cylinder 4 directly forms the cylindrical reflecting surface. In the exemplary embodiment shown, however, the interior wall surface is provided with an additional reflective layer 5 having optimal reflecting properties, which layer creates the cylindrical reflecting surface.

In the direction of the photodetector 2, a fluorescent light filter 6 is connected to the hollow cylinder 4, which filter allows the fluorescent light to pass that is to be measured by the cells. The photodetector 2 is located behind the fluorescent light filter 6. On the side of the flow-through cuvette 8 opposite the photodetector 2, the cuvette window is provided with a reflective layer 7. The efficacy of the light collected is thus increased.

Figure 2:
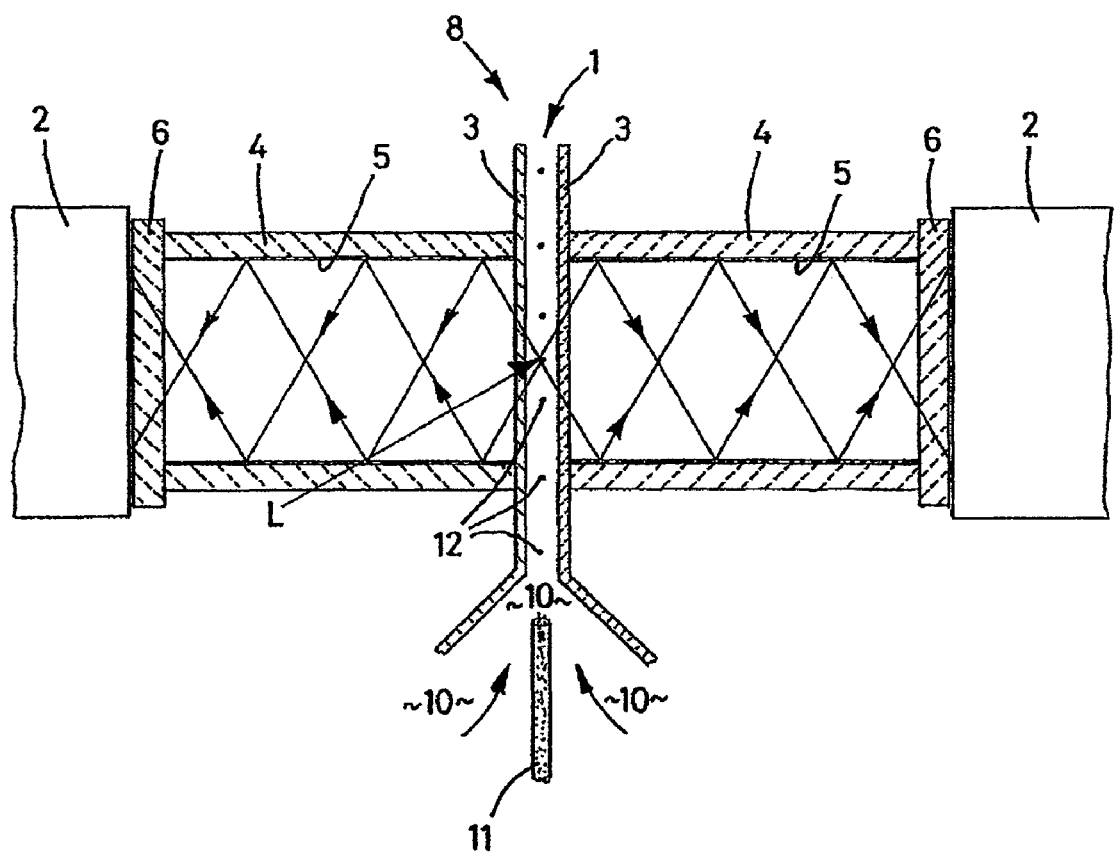

With a further exemplary embodiment according to FIG. 2, an independent measuring device is respectively arranged on both sides of the flow-through cuvette 8, which devices are both embodied according to FIG. 1: correspondingly, they have two internally mirrored hollow cylinders 4, fluorescent light filters 6 and photodetectors 2. By using two different fluorescent light filters 6, different light wavelengths can thus be recorded in a single measuring step.

Figure 3:
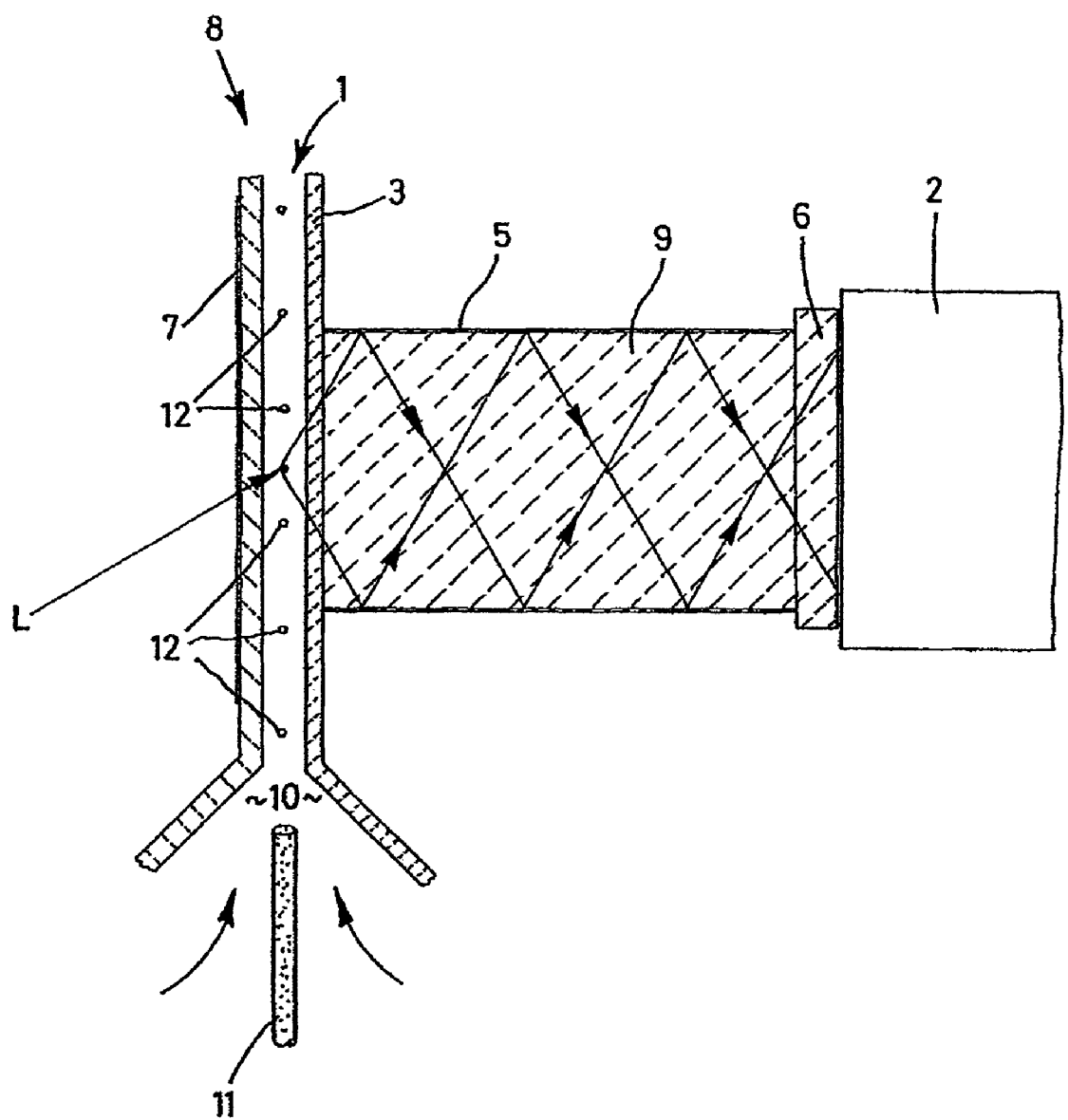

In a further exemplary embodiment according to FIG. 3 it is provided that the cylindrical reflecting surface is not formed by an internally mirrored hollow cylinder, but by a solid cylinder 9 in the form of a glass rod that is mirrored externally, and the exterior diameter of which corresponds to the interior diameter of the hollow cylinder 4 of FIG. 1. The reflective layer 5, applied externally in this case, forms the cylindrical reflecting surface and can be provided with a protective layer (not shown for reasons of clarity), e.g., a protective varnish, which protects the reflective layer from atmospheric exposure. Similar to the exemplary embodiment of FIG. 2, the arrangement of two measuring devices can also be provided with a device according to FIG. 3, which measuring devices in this case contain solid cylinders 9, respectively.

It is respectively provided with all of the devices to protect the measuring devices and in particular the cylinders 4 and 9 from mechanical influences by a housing (not shown in the drawings).

FIG. 1 indicates a solid angle 14 of the fluorescent light to be recorded. This solid angle 14 is essentially determined by the total reflection angle at the interfaces of liquid and glass wall in the interior channel 1 and window 3. As a result, the distance of the particle to be measured from the light-collecting hollow cylinder 4 is noncritical. The mirrored light-collecting hollow cylinder 4 has a comparatively large diameter. As a result, the position of the particle to be measured perpendicular to the observation direction is noncritical as well.

Irrespective of the position of the particle, the light from the same solid angle 14 of the fluorescent light always reaches the hollow cylinder 4.

The invention claimed is:

1. A device for measuring fluorescent light or scattered light emitted by microscopically small particles or cells, with a flow-through cuvette through which luminescent particles or cells are guided, whereby the flow-through cuvette has a transparent window, and with a photodetector, which records light emitted by the luminescent particles or cells, and with an optical element that guides light emerging from the window to the photodetector, characterized in that the optical element is embodied as a cylinder with a cylindrical reflecting surface.

2. The device according to claim 1, wherein the cylinder is embodied as a hollow cylinder, the interior surface of which forms the cylindrical reflecting surface.

3. The device according to claim 1, wherein the cylinder is embodied as a solid, transparent cylinder, the exterior surface of which forms the cylindrical reflecting surface.

4. The device according to claim 1, wherein a fluorescent light filter transparent to fluorescent light is located between the flow-through cuvette and the photodetector.

5. The device according to claim 4, wherein fluorescent light filters are arranged on both sides of the flow-through cuvette, whereby the two fluorescent light filters are transparent to different light wavelengths.

6. The device according to claim 1, wherein an independent light-measuring arrangement is respectively located on two sides of the flow-through cuvette, which arrangements are equipped with different filters transparent merely to fluorescent light.

7. The device according to claim 1, wherein the cylindrical reflecting surface of the cylinder has a circular cross section.

8. The device according to claim 1, wherein the cylinder has a high numerical aperture.

9. The device according to claim 8, wherein the diameter of the cylindrical reflecting surface is at least big enough to allow the share of light emitted by a particle or a cell within the maximum solid angle theoretically possible and limited by the total reflection in the area of the flow-through cuvette, to reach as completely as possible the interior space enclosed by the cylindrical reflecting surface.

10. The device according to claim 1, wherein the cylindrical reflecting surface is formed by a coating of the cylinder.

11. A device for measuring light emitted by luminescent particles or cells, comprising:
 a flow-through cuvette;
 a photodetector structured and arranged to record the light emitted by the luminescent particles or cells;
 an optical element, comprising a cylindrical reflecting surface, being structured and arranged to guide the emitted light to the photodetector.

12. The device according to claim 11, wherein the flow-through cuvette is structured so that the luminescent particles or cells are guided through the cuvette.

13. The device in accordance with claim 11, wherein the flow-through cuvette includes a transparent window.

14. The device in accordance with claim 13, wherein the optical device is arranged to guide light of the emitted light passing through the transparent window to the photodetector.

\* \* \* \* \*